(12) United States Patent
L'Italien et al.

(10) Patent No.: US 7,312,196 B2
(45) Date of Patent: Dec. 25, 2007

(54) FORMULATIONS FOR AMYLIN AGONIST PEPTIDES

(75) Inventors: James L'Italien, Del Mar, CA (US); Gregg Stetsko, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/159,779

(22) Filed: May 31, 2002

(65) Prior Publication Data

US 2003/0092606 A1 May 15, 2003

Related U.S. Application Data

(63) Continuation-in-part of application No. 09/005,262, filed on Jan. 9, 1998, now Pat. No. 6,410,511.

(51) Int. Cl.
*A61K 38/00* (2006.01)
*A61K 47/00* (2006.01)

(52) U.S. Cl. ............ 514/12; 514/2; 514/3; 514/4; 514/866; 514/864; 424/400; 530/324

(58) Field of Classification Search ............ 514/12, 514/2, 3, 866, 864; 424/400; 530/324
See application file for complete search history.

(56) References Cited

U.S. PATENT DOCUMENTS

| | | | |
|---|---|---|---|
| 4,654,324 A | 3/1987 | Chance et al. | 514/12 |
| 5,124,314 A | 6/1992 | Cooper | 514/4 |
| 5,175,145 A | 12/1992 | Cooper | 514/4 |
| 5,234,906 A * | 8/1993 | Young et al. | 514/12 |
| 5,266,561 A | 11/1993 | Cooper et al. | 514/12 |
| 5,280,014 A | 1/1994 | Cooper et al. | 514/12 |
| 5,281,581 A | 1/1994 | Cooper et al. | 514/12 |
| 5,364,841 A | 11/1994 | Cooper et al. | 514/12 |

(Continued)

FOREIGN PATENT DOCUMENTS

WO    WO 93/10146    5/1993

(Continued)

OTHER PUBLICATIONS

Ratner et al. Less hypoglycemia with insulin glargine in intensive insulin therapy for type I diabetes. U.S. study Group iof Insulin Glargine in Type I diabetes. Diabetes Care . May 2000, 23(5):639-643.*

(Continued)

*Primary Examiner*—Lakshmi S. Channavajjala
(74) *Attorney, Agent, or Firm*—Intellectual Property Group (57) ABSTRACT

The present invention is concerned with a pharmaceutical formulation comprising an amylin agonist and optionally a buffer, a tonicifier or stabilizer, and a preservative in a container, for example, a vial, prefilled cartridge, prefilled syringe or disposable pen. This formulation may be in liquid, gel, solid or powdered form for delivery, for example, via nasal, pulmonary, oral, sublingual, buccal, transdermal, or parenteral routes. Formulation with biocompatible polymers and release modifiers, such as sugars, can facilitate controlled release after injection, minimizing the number of administrations to a patient. These formulations maintain stability upon storage under refrigerated or room temperature conditions. Such formulations can be further combined with insulin for administration to a patient.

28 Claims, 3 Drawing Sheets

U.S. PATENT DOCUMENTS

| | | | | |
|---|---|---|---|---|
| 5,367,052 | A | 11/1994 | Cooper et al. | 530/307 |
| 5,503,827 | A | 4/1996 | Woog et al. | 424/85.1 |
| 5,508,260 | A | 4/1996 | Beaumont | 514/4 |
| 5,686,411 | A | 11/1997 | Gaeta et al. | 514/12 |
| 5,783,556 | A | 7/1998 | Clark et al. | 514/4 |
| 5,791,466 | A | 8/1998 | Tsals | 206/222 |
| 6,136,784 | A * | 10/2000 | LItalien et al. | 514/12 |
| 6,410,511 | B2 * | 6/2002 | L'Italien et al. | 514/12 |

FOREIGN PATENT DOCUMENTS

| | | |
|---|---|---|
| WO | WO 96/40196 | * 12/1996 |
| WO | WO 96/40220 | 12/1998 |
| WO | WO 98/55144 | 12/1998 |

OTHER PUBLICATIONS

Zhou et al. Peptide and protein drugs:I. Therapeutic applications, absorption and parenteral administration. International Journal of Pharmaceutics, (1991), vol. 75, pp. 97-115.*

Ratner et al. Les hypoglemia with insulin glargine in intensive insulin therapy for type I diabetes. U.S.Study group of insulin glargfine in Type I diabetes. Diabetes Care 2000. vol. 23 (5): pp. 576-578. abstract only.*

Amylin Pharmaceuticals. "Amylin Pharmaceuticals Announces Positive Positive Clinical Results in Mixing Its Experimental Diabetes Drug with Insulin" Amylin Pharmaceuticals Press Release, San Diego, California (Jan. 8, 1997).

Arakawa et al. "Change in Solubility of Insulin in Therapeutic Mixtures of Insulin Preparations: HPLC Analysis" Diabetes Research and Clinical Practice 7:S93-S100 (1989).

Avis et al. (Ed.) *Pharmaceutical Dosage Forms: Parenteral Medications* vol. 1, $2_{nd}$ Ed., Mercel Dekker, New York, N.Y. (1992).

Brange et al. "Insulin Structure and Stability" in Stability and Characterization of Protein and Peptide Drugs: Case Histories (1993).

Colowick et al. (Eds.) *Methods in Enzymology* vol. 1 Academic Press Inc., Publishers, NY pp. 13146 (1955).

Cooper et al. "Purification and Characterization of a Peptide from Amyloid-Rich Pancreases of Type 2 Diabetic Patients" Proceedings of the National Academy of Sciences USA 84(23):8628-8632 (1987).

Deshmukh et al. "Simulated Patient-Use Patterns and Temperature Excursion Studies on Pramlintide Injection Final Drug Product" Pharmaceutical Research 14 (11 Supp): S469-S470 (1997) (Abstract 3022).

Gaeta and Rink. "Amylin: A New Hormone as a Therapeutic Target in Diabetes Mellitus and Other Metabolic Diseases" Med. Chem. Res. 3:483-490 (1994).

Gennaro (Ed.) *Remington's Pharmaceutical Sciences* $18^{th}$ Ed. Mack Publishing Co. pp. 1545-1553 (1990).

Hekman et al. "Isolation and Identification of Cyclic Imide and Deamidation Products in Heat Stress Pramlintide Injection Drug Product" J Pharm & Biomed Analysis 20(5):763-772 (1999).

Kenley et al. "Kinetics of Pramlintide Degradation in Aqueous Solution As a Function of Temperature and pH" AAPS Pharmscitech 1(2):article 7 (Apr. 21, 2000).

Kenley et al. "Pramlintide Injection Drug Product Robustness Studies" AAPS Pharmscitech 1(2):article 8 (Apr. 21, 2000).

Kolterman et al. "Effect of 14 Days' Subcutaneous Administration of the Human Amylin Analogue, Pramlintide (AC137), on an Intravenous Insulin Challenge and Response to a Standard Liquid Meal in Patients with IDDM" Diabetologia 39(4):492-499 (1996).

Leighton et al. "The Role of Amylin in the Insulin Resistance of Non-Insulin-Dependent Diabetes Mellitus" TIBS 15:295 (1990).

Manning et al. "Stability of Protein Pharmaceuticals" Pharmaceutical Research 6(11):903-918 (1989).

Mlodzik. "Oncologic, Endocrine & Metabolic Antidiabetes: Analysis of Patenting 1990-199" Exp. Opin Ther. Patents 5(7):685-688 (1995).

Pittner et al. "Molecular Physiology of Amylin" J. Cell Biochem. 55S:19-28 (1994).

Rink et al. "Structure and Biology of Amylin" TIPS 14:113-118 (1993).

Sifton (Ed.) *Physician's Desk Reference* $50^{th}$ Ed. pp. 1797-1800 (1996).

Wang et al. "Parental Formulations of Proteins and Peptides: Stability and Stabilizers" J. Parenteral Science and Technology Supplement 42S:S4-S26 Technology Report No. 10 (1988).

Wang et al. "Review of Excipients and pH's for Parenteral Products Used in the United States" J. Parenteral Drug Assoc. 34:452 (1980).

* cited by examiner

FORMULATIONS FOR AMYLIN AGONIST PEPTIDES

This application is a continuation in part of U.S. Ser. No. 09/005,262, filed Jan. 9, 1998, now issued as U.S. Pat. No. 6,410,511, issued Jun. 25, 2002.

FIELD OF INVENTION

This invention relates to pharmaceutical formulations of amylin agonist peptides, particularly in solid, suspension and liquid formulations. Additionally, this invention relates to amylin agonist pharmaceutical formulations which are compatible upon mixing with insulin or are prepared to allow co-administration with insulin or other therapeutic or antidiabetic compositions.

BACKGROUND OF THE INVENTION

Deposition of amyloid in pancreatic islets is a common feature in human Type II diabetic patients. The major protein forming these amyloid particles, called amylin, has a propensity to form fibril amyloid structures. *Proceedings of the National Academy of Sciences USA* 84(23):8628-32, 1987. Amylin is a 37 amino acid protein which, in its fully active form, is carboxy-amidated and has a disulfide bridge between the cysteine residues found at positions 2 and 7. Amylin plays a role in control of systemic concentrations of glucose, and has been proposed as a useful therapeutic agent. See, e.g., Leighton and Cooper, 15 *TIBS* 295, 1990. Human amylin is described and claimed in U.S. Pat. No. 5,367,052, entitled "Amylin Peptides," and U.S. Pat. No. 5,124,314, entitled "Pharmaceutical Compositions Containing Amylin." Amylin has been reviewed in the literature, for example, in Gaeta, L. S. L. and Rink, T. J., 3 *Med. Chem. Res.* 483-490, 1994, Pittner, R. A. et al., 55S *J. Cell. Biochem.* 19-28, 1994, and Rink, T. J. et al., 14 *TIPS* 113-118, 1993.

Therapeutic opportunities for insulin-using and other people with diabetes who are deficient in amylin or for whom amylin therapy would be of benefit, and hormone blockage for other people, for example, the obese and Type II diabetics and those with insulin resistance who may have elevated plasma amylin or undesired amylin activity have been pursued. The use of amylin agonists, including amylin itself, for the treatment of diabetes is described and claimed in U.S. Pat. No. 5,175,145. The use of amylin antagonists for the treatment of Type II diabetes mellitus, obesity and essential hypertension, and insulin resistance, are described and claimed in U.S. Pat. Nos. 5,266,561, 5,280,014, 5,281,581, and 5,364,841.

The most severe form of the disease is Type I (juvenile-onset) diabetes. There are an estimated 1 million Type I diabetics in the U.S. who need daily insulin injections for survival. Their quality of life is often markedly affected by the rigors of their daily metabolic imbalances, in particular hypoglycemic attacks (dangerously low blood glucose) and by the onset of serious long-term complications, including blindness, kidney failure, impotence, ulcers, amputations and atherosclerosis (NIH Diabetes Complications and Control Trial).

Type II (adult-onset) diabetes afflicts over 10 million Americans, who are also subject to the same complications. Impaired glucose tolerance, a risk factor for Type II diabetes and cardiovascular disease, is thought to affect another 20 million people in the U.S. and is not treatable by any known regimen. There is also an alarming increase in the incidence of Type II diabetics in groups of populations around the world, whose standard of living is increasing through economic development or migration. Sulfonylureas are the primary oral antihyperglycemic diabetic medications sold in the U.S. Discovered in the 1940's, these compounds do not address the underlying causes of Type II diabetes and, in many cases, are not effective or lose their efficacy after a few years of treatment. Type II diabetics do not lack insulin, rather they are insulin resistant, so that insulin does not work properly and the insulin secretory responses are disordered.

After a meal, the pancreas secretes insulin in response to a rise in glucose. Insulin stimulates the uptake of glucose into muscle and fat, and signals the liver to reduce glucose production; this results in a return of blood glucose to normal levels. In muscle, large amounts of glucose are stored as glycogen. Some of the glycogen is broken down into lactate, which circulates to the liver and can be converted back into glucose and stored as glycogen. Between meals the liver breaks down these glycogen stores to provide glucose to the brain and other tissues. This cycle in which glycogen is effectively transferred from muscle to liver is known as the Cori cycle. The stimulus for this flux from muscle to liver under resting conditions remain unidentified; recent results indicate that amylin provides a major stimulus to this pathway.

Amylin has been demonstrated to have direct metabolic effects in both skeletal muscle and the pancreas. In skeletal muscle, amylin acts as a non-competitive antagonist of insulin, reducing insulin-stimulated incorporation of glucose into glycogen. In vitro studies indicate that amylin reduces glycogen synthese activity and favors the formation of an active form of glycogen phosphorylase, the enzyme that converts glycogen into glucose 6-phosphate. The actions of amylin on skeletal muscle promote glycogen breakdown, thus stimulating lactate formation and increasing turnover of the Cori cycle. Amylin is co-secreted with insulin from pancreatic beta cells and has been demonstrated to suppress insulin secretion. It appears to provide feedback regulation of the beta-cell, in order to modulate insulin secretory activity.

It is believed that amylin plays a role in the regulation of glucose uptake from ingested food into blood, and that amylin or amylin agonist therapy in diabetics, particularly insulin-using diabetics, such as Type I diabetics and late-stage Type II diabetics, will smooth the excessive glucose rises that these patients typically experience after meals. Deficiency of an important hormone such as amylin which has been reported to have effects on carbohydrate, fat and bone metabolism, may also disrupt other important physiological mechanisms. The co-administration of amylin, or an amylin agonist which exerts the physiological effects of amylin, will significantly improve existing insulin therapy by restoring the appropriate metabolic balance.

Many factors affect the stability of a pharmaceutical product, including the chemical reactivity of the active ingredient(s), the potential interaction between active and inactive ingredients, the manufacturing process, the dosage form, the container-closure system, and the environmental conditions encountered during shipment, storage, handling and length of time between manufacture and usage. Pharmaceutical product stability is determined by the chemical stability as well as the physical stability of the formulation. Physical factors including heat and light may initiate or accelerate chemical reactions.

Optimal physical stability of a formulation is very important for at least three primary reasons. First, a pharmaceutical product must appear fresh, elegant and professional, when it is administered to a patient. Any changes in physical appearance such as color changes or haziness can cause a patient or consumer to lose confidence in the product. Second, because some products are dispensed in multiple-dose containers, uniformity of dose content of the active ingredient over time must be assured. A cloudy solution or a broken emulsion can lead to a non-uniform dosage pattern. Third, the active ingredient must be available to the patient throughout the expected shelf life of the preparation. A breakdown of the product to inactive or otherwise undesired forms can lead to non-availability of the medicament to the patient.

Stability of a pharmaceutical product, then, may be defined as the capability of a particular formulation to remain within its physical, chemical, microbiological, therapeutic and toxicological specifications. A stable solution retains its original clarity, color and odor throughout its shelf life. Retention of clarity of a solution is a main concern in maintaining physical stability. Solutions should remain clear over a relatively wide temperature range such as about 4° C. to about 37° C. At the lower range an ingredient may precipitate due to a lower solubility at that temperature, while at higher temperatures homogeneity may be destroyed by extractables from the glass containers or rubber closures. Thus, solutions of active pharmaceutical ingredients must be able to handle cycling temperature conditions. Similarly, a formulation should retain its color throughout this temperature range, and its odor should be stably maintained.

Small peptides are typically unstable and are susceptible to degradation in aqueous solution. In this regard, once a human amylin agonist or amylin has less than approximately 90% of its labeled potency, it is no longer considered to be suitable for administration to a patient. Various types of molecules such as sugars, surfactant, amino acids and fatty acids, used singly or in combination, have been used in efforts to stabilize protein and peptide products against degradation. See Wang and Hanson, *J. Parenteral Science and Technology Supplement*, 1988, Technical Report No. 10 (describing parenteral formulations of proteins and peptides); Manning et al., 6 *Pharmaceutical Research*, 1989. Examples of excipients such as buffers, preservatives, isotonic agents, and surfactants are also known in the art. See 21 C.F.R. §180.22 et seq. (defining recognized food additives); Wang and Kowal, 34 *J. Parenteral Drug Association* 452, 1980 (describing various excipients); A. R. Gennaro et al., 17th Remington's "Pharmaceutical Sciences," 1985; Avis et al., Pharmaceutical Dosage Forms: Parenteral Medications, Vol. 1, 1992, all of which, including the definitions of various useful excipients, are hereby incorporated by reference herein.

SUMMARY OF THE INVENTION

The inventors have discovered novel pharmaceutical formulations and dosage forms useful for the administration of amylin agonist peptides to a patient or subject in need of treatment with such compounds. These dosage forms include approximately 0.01 to 1.0% (w/v), preferably 0.5 to 1.0%, respectively, of an amylin agonist, or amylin, as the active ingredient in an aqueous system. This concentration may vary based upon mode of administration and type of formulations, however, formulations of the present description, whether liquid or solid, may contain amylin or amylin agonist in a concentration range from about 0.01 (w/w) to about 98% (W/W).

The amylin or amylin agonist is frequently included along with approximately 0.02 to 0.5% (w/v) of an acetate, phosphate, citrate or glutamate buffer to obtain a pH of the final composition of about 3.0 to about 7.0, as well as approximately 1.0 to 10% (w/v) of a carbohydrate or polyhydric alcohol tonicifier in an aqueous continuous phase, provided, however, that if the amylin agonist or amylin has similar physiochemical characteristics similar to those of human amylin, it should be formulated and lyophilized for storage (and used immediately upon reconstitution). Approximately 0.005 to 1.0% (w/v) of an antimicrobial preservative selected from the group consisting of m-cresol, benzyl alcohol, methyl, ethyl, propyl and butyl parabens and phenol may also be present in the formulation of product designed to allow the patient to withdraw or administer multiple doses. Importantly, a stabilizer is not required in this amylin agonist product formulation. A sufficient amount of a liquid vehicle, such as water for injection may be used to obtain the desired concentration of solution. Sodium chloride, as well as other excipients, may also be present, if desired. Such excipients, however, must maintain the overall stability of the amylin agonist or amylin peptide.

The liquid formulations of the invention should be substantially isotonic. An isotonic solution may be defined as a solution that has a concentration of electrolytes, non-electrolytes, or a combination of the two that will exert equivalent osmotic pressure as that into which it is being introduced, here, for example in the case of parenteral injection of the formulation, a mammalian tissue. By "substantially isotonic" is meant within ±20% of isotonicity, preferably within ±10%. The formulated product is included within a container, typically, for example, a vial, cartridge, prefilled syringe, or a two chambered syringe, cartridge or disposable pen injector.

It has been found that this novel parenteral dosage form surprisingly maintains the stability of the peptide for up to four years at refrigerated temperatures, e.g., approximately 5° C., and over 30 days at room temperature, e.g., approximately 30° C.

The inventors have further discovered that the above described pharmaceutical formulation can be further mixed with insulin product and retain short term stability. This mixture may occur, e.g., in a syringe. This short term mixing compatibility is extremely advantageous. This allows administration of a single injection of an amylin agonist, or amylin, along with insulin to a patient.

This invention describes formulations of amylin agonists, or amylins, which are stabilized with respect to aggregation, adsorption and degradation, and thus enhance preservation of their biological activities, although formulations of either an amylin agonist or an amylin which has physicochemical properties similar to those of human amylin, which is poorly soluble and highly unstable should also include a stabilizer, comprising 1.0 to 10% (w/v) of a carbohydrate or a polyhydric alcohol, and a surfactant, preferably about 0.05 to about 1.0% (w/v) of polysorbate 80 or other non-ionic detergent, should be lyophilized promptly after formulation, and should be used promptly upon reconstitution and are therefore less preferred. Generally, the presently described formulations may be lyophilized according to methods known in the art.

A further aspect of the invention features a formulation including an amylin agonist, mixed with a stabilizing compound which reduces loss of biological potency of the peptide in, for example, an amylin specific receptor binding assay, reduces loss of biological activity as measured in, for example, the in vitro soleus muscle bioassay, and general loss of material by, for example, an HPLC assay, as compared to a formulation consisting of the amylin alone.

In a related aspect, the invention features a method for formulating amylin agonists that retain short term (e.g., up to 24 hours) mixing compatibility with insulin. Certain insulins, such as insulin glargine (Lantus®), may allow for longer term stability (the term "insulin," as used in the presently described formulations, refers to various types of insulins including, for example, insulin glargine).

In another aspect, the present disclosure provides therapeutic methods for treating patients, for example, a method for treating a diabetic patient in need of such treatment comprising administering a therapeutically effective amount of an amylin or amylin agonist formulation described herein.

Other features and advantages of the invention will be apparent from the following description of the preferred embodiments thereof, and from the claims.

DETAILED DESCRIPTION

It is understood that the development of a suitable pharmaceutical formulation for administration to a subject is complex. A need exists in the art for pharmaceutical formulations of amylin agonist peptides, or amylins (both are also referred to herein as "peptides"), designed to provide single or multiple doses having substantial stability when refrigerated and at room temperature. Further, a need exists in the art for a liquid pharmaceutical formulation packaged with a container/closure system that also minimizes the physical and chemical degradation of such peptides. Liquid formulations are suitable for, e.g., injection, nasal or pulmonary delivery. A need also exists for a pharmaceutical formulation for amylin agonist peptides, or amylins, which can be mixed with insulin or other therapeutics, such as antidiabetic agents prior to administration. The mixture of the amylin or amylin agonist with insulin may be simultaneous, in either order or concerted and sequential. In addition, this mixture may occur prior to preparing the presently described formulations, concurrently therewith or at a later time. Other formulations, such as solid dosage forms (including powders), allow for administration to a subject via oral, pulmonary, sublingual or buccal routes. Formulations that entrap or coat the desired peptide in a polymer, wax or fatty material are suitable for controlled release. See e.g., U.S. Pat. No. 6,368,630 and related patents, U.S. Pat. No. 6,379,704 and related patents. Formulations which are produced in a fine, solid particulate form (fine powders) may be suitable for pulmonary or nasal delivery. Formulations that incorporate the desired peptide in a patch or device are suitable for transdermal delivery. The invention described and claimed herein meets these needs.

Peptide drugs undergo physical and chemical degradation in solution, and lose their biological activity. A preferred dosage form reported in this invention minimizes the chemical degradation of amylin, for example, pramlintide, through different pathways, for example, deamination and peptide bond hydrolysis, and keeps the peptide biologically active for up to four years when stored at approximately 5° C. This dosage form is well-tolerated by patients. The container/closure system used to store this formulation also minimizes the physical loss of drug product through adsorption onto the container surface or adsorption into the rubber closure.

People with Type I diabetes must be treated with exogenous insulin. Generally, persons who initially require insulin tend to be younger than 30 years of age at the time of diagnosis, lean, prone to developing ketoacidosis, and markedly hyperglycemic even in the fasting state. Insulin is also indicated for Type II diabetics who do not respond to diet and exercise therapy either alone or in combination with oral hypoglycemic drugs. Insulin therapy is also necessary in some Type II diabetic patients who are subject to stresses such as infections, pregnancy, or surgery. In Type II diabetics, doses of 10-20 units of intermediate-acting insulins are occasionally needed to bring hyperglycemia under control.

Any functional macromolecular component of a patient may serve operationally as a drug receptor. A particularly important group of drug receptors are proteins that normally serve as receptors for endogenous regulatory ligands (e.g., hormones, neurotransmitters). Many drugs act on such physiological receptors. Those that mimic the effects of the endogenous regulatory compound are termed agonists.

By "amylin agonist" is meant peptide analogues of human amylin useful as agonists of amylin, including but not limited to those amylin agonists which are represented by the formula wherein $A_1$ is hydrogen Lys, Ser, Ala, des-α-amino Lys, or acetylated Lys; $B_1$ is Ala, Ser or Thr; $C_1$ is Val, Leu or Ile; $D_1$ is His or Arg; $E_1$ is Ser or Thr; $F_1$ is Ser, Thr, Gln or Asn; $G_1$ is Asn, Gln or His; $H_1$ is Phe, Leu or Tyr; $I_1$ is Ala or Pro; $J_1$ is Ile, Val, Ala or Leu; $K_1$ is Ser, Pro, Leu, Ile or Thr; $L_1$ is Ser, Pro or Thr; $M_1$ is Asn, Asp or Gln; X and Y are independently selected residues having side chains which are chemically bonded to each other to form an intramolecular linkage; and Z is hydroxy, amino, alkylamino, dialkylamino, cycloalkylamino, arylamino, aralkylamino, alkyloxy, aryloxy or aralkyloxy; provided that (a) when $A_1$ is Lys, $B_1$ is Ala, $C_1$ is Val, $D_1$ is His, $E_1$ is Ser, $F_1$ is Ser, $G_1$ is Asn, $H_1$ is Phe, $I_1$ is Ala, $J_1$ is Ile, $K_1$ is Ser, $L_1$ is Ser, and $M_1$ is Asn; (b) when $A_1$ is Lys, $B_1$ is Ala, $C_1$ is Ile, $D_1$ is Arg, $E_1$ is Ser, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (c) when $A_1$ is Lys, $B_1$ is Ala, $C_1$ is Val, $D_1$ is Arg, $E_1$ is Thr, $F_1$ is Ser, $G_1$ is Asn, $H_1$ is Leu, $I_1$ is Ala, $J_1$ is Ile, $K_1$ is Ser, $L_1$ is Pro, and $M_1$ is Asn; (d) when $A_1$ is Lys, $B_1$ is Ala, $C_1$ is Val, $D_1$ is Arg, $E_1$ is Ser, $F_1$ is Ser, $G_1$ is Asn, $H_1$ is Leu, $I_1$ is Pro, $J_1$ is Val, $K_1$ is Pro, $L_1$ is Pro, and $M_1$ is Asn; (e) when $A_1$ is Lys, $B_1$ is Ala, $C_1$ is Val, $D_1$ is His, $E_1$ is Ser, $F_1$ is Asn, $G_1$ is Asn, $H_1$ is Leu, $I_1$ is Pro, $J_1$ is Val, $K_1$ is Ser, $L_1$ is Pro and $M_1$ is Asn; or (f) when $A_1$ is Lys, $B_1$ is Thr, $C_1$ is Val, $D_1$ is Arg, $E_1$ is Ser, $F_1$ is Ser, $G_1$ is His, $H_1$ is Leu, $I_1$ is Ala, $J_1$ is Ala, $K_1$ is Leu, $L_1$ is Pro and $M_1$ is Asp; then one or more of any of $A_1$ to $M_1$ is not an L-amino acid and Z is not amino, it being further noted that single-proline substituted peptides at $I_1$, $K_1$, and $L_1$ are not preferred.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

As used herein, the following terms have the following meanings unless expressly stated to the contrary: The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like. The term "aryl" refers to carbocyclic aromatic groups of 6 to 14 carbon atoms such as phenyl and naphthyl, as well as heterocyclic aromatic groups containing 1 to 3 heteroatoms (nitrogen, oxygen, sulfur, etc.) such as pyridyl, triazolopyrazine, pyrimidine and the like. The term "aralkyl" refers to an "aryl" group of 6 to 10 carbon atoms directly attached to an "alkyl" group of 1 to 4 carbon atoms and includes for example benzyl, p-chlorobenzyl, p-methylbenzyl, and 2-phenylethyl. The term "cycloalkyl" refers to cyclic alkyl groups of 5 to 8 carbon atoms.

Biologically active derivatives of the above formula agonist analogues are also included in which the stereochemistry of individual amino acids may be inverted from (L)/S to (D)/R at one or more specific sites. Also included are the agonist analogues modified by glycosylation of Asn, Ser and/or Thr residues.

Biologically active agonist analogues of amylin are included which contain less peptide character. Such peptide mimetics may include, for example, one or more of the following substitutions for —CO—NH— amide bonds: depsipeptides (—CO—O—), iminomethylenes (—$CH_2$—NH—), trans-alkenes (—CH=CH—), -enaminonitriles (—C(=CH—CN)—NH—), thioamides (—CS—NH—), thiomethylenes (—S—$CH_2$— or —$CH_2$—S—), methylenes ($CH_2$—$CH_2$—) and retro-amides (NH—CO—).

Amylin agonist compounds form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). Acetate, hydrochloride, and trifluoroacetate salts are preferred.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Amylin agonist compounds include various stereoisomers. In the preferred compounds of this invention, the chiral centers on the peptide backbone are all S.

Amylin agonists may be prepared by those of ordinary skill in the art, as described in "Amylin Agonist Peptides and Uses Therefor," U.S. Pat. No. 5,686,411, the contents of which is hereby incorporated by reference in its entirety.

By "human amylin" is meant the 37 amino acid amylin set forth in U.S. Pat. No. 5,357,052.

The nomenclature of the compounds of the present invention can be used to indicate both the peptide that the sequence is based on and the modifications made to any basic peptide amylin sequence, such as human amylin. An amino acid preceded by a superscript number indicates that the named amino acid replaces the amino acid normally present at the amino acid position of the superscript in the basic amino acid sequence. For example, "$^{18}$Arg$^{25,28}$Pro-h-amylin" refers to a peptide based on the sequence of "h-amylin" or "human-amylin" having the following substitutions: Arg replacing His at residue 18, Pro replacing Ala at residue 25 and Pro replacing Ser at residue 28. The term "des-$^1$Lys-h-amylin" refers to a peptide based on the sequence of human amylin, with the first, or N-terminal, amino acid deleted.

In addition to the description of compounds pursuant to the above formula, certain preferred compounds may be identified, including $^{25,28,29}$Pro-h-amylin, $^{18}$Arg$^{25,28}$Pro-h-amylin, des-$^1$Lys$^{18}$Arg$^{25,28}$Pro-h-amylin, des-$^1$Lys-h-amylin and $^{25}$Pro$^{26}$Val$^{28,29}$Pro-h-amylin. These peptides preferably have a reduced tendency to form aggregates or to precipitate under pressure compared to human amylin.

Compounds described herein which are especially preferred include $^{18}$Arg$^{25,28}$Pro-h-amylin, des-$^1$Lys$^{18}$Arg$^{25,28}$Pro-h-amylin, $^{18}$Arg$^{25,28,29}$Pro-h-amylin, des-$^1$Lys$^{18}$rg$^{25,28,29}$ Pro-h-amylin, $^{25,28,29}$Pro-h-amylin, des-$^1$Lys$^{25,28,29}$ Pro-h-amylin, and $^{25}$Pro$^{26}$Val$^{25,28}$Pro-h-amylin. Still further amylin agonist peptide compounds include:

$^{23}$Leu$^{25}$Pro$^{26}$Val$^{28,29}$Pro-h-amylin;
$^{23}$Leu$^{25}$Pro$^{26}$Val$^{28}$Pro-h-amylin;
des-$^1$Lys$^{23}$Leu$^{25}$Pro$^{26}$Val$^{28}$Pro-h-amylin;
$^{18}$Arg$^{23}$Leu$^{25}$Pro$^{26}$Val$^{28}$Pro-h-amylin;
$^{18}$Arg$^{23}$Leu$^{25,28,29}$Pro-h-amylin;
$^{18}$Arg$^{23}$Leu$^{25,28}$pro-h-amylin;
$^{17}$Ile$^{23}$Leu$^{25,28,29}$Pro-h-amylin;
$^{17}$Ile$^{25,28,29}$Pro-h-amylin;
des-$^1$Lys$^{17}$Ile$^{23}$Leu$^{25,28,29}$Pro-h-amylin;
$^{17}$Ile$^{18}$Arg$^{23}$Leu-h-amylin;
$^{17}$Ile$^{18}$Arg$^{23}$Leu$^{26}$Val$^{29}$Pro-h-amylin;
$^{17}$Ile$^{18}$Arg$^{23}$Leu$^{25}$Pro$^{26}$Val$^{28,29}$Pro-h-amylin;
$^{13}$Thr$^{21}$His$^{23}$Leu$^{26}$Ala$^{28}$Leu$^{29}$Pro$^{31}$Asp-h-amylin;
$^{13}$Thr$^{21}$His$^{23}$Leu$^{26}$Ala$^{29}$Pro$^{31}$Asp-h-amylin;
des-$^1$Lys$^{13}$Thr$^{21}$His$^{23}$Leu$^{26}$Ala$^{28}$Pro$^{31}$Asp-h-amylin;
$^{13}$Thr$^{18}$Arg$^{21}$His$^{23}$Leu$^{26}$Ala$^{29}$Pro$^{31}$Asp-h-amylin;
$^{13}$Thr$^{18}$Arg$^{21}$His$^{23}$Leu$^{28,29}$Pro$^{31}$Asp-h-amylin; and,
$^{13}$Thr$^{18}$Arg$^{21}$His$^{23}$Leu$^{25}$Pro$^{26}$Ala$^{28,29}$Pro$^{31}$Asp-h-amylin.

$^{25,28,}$29Pro-h-amylin which is also referred to as "pramlintide," is a particularly preferred agonist of human amylin. $^{25,28,29}$pro-h-amylin will be referred to as "pramlintide" hereafter. Pramlintide is substantially different from and better than human amylin, retaining the desired biological properties of human amylin with superior attributes, including superior pharmaceutical properties (L. S. L. Gaeta and T. J. Rink, *Medicinal Chemistry Research,* 1994). Pramlintide and other amylin agonists set forth herein are described and claimed in U.S. Pat. No. 5,686,411, issued Nov. 11, 1997.

Amylin agonists may be formulated into a stable, safe pharmaceutical composition for administration to a patient. The novel pharmaceutical formulations of the present invention may comprise approximately 0.01 to 1.0% (w/v), preferably 0.05 to 1.0%, of an amylin agonist, or amylin, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In a particular embodiment of the present invention, a pharmaceutical formulation of the present invention may contain a range of concentrations of amylin agonist, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in this embodiment. A sufficient amount of water for injection may be used to obtain the desired concentration of solution.

Additional tonicifying agents such as sodium chloride, as well as other known excipients, may also be present, if desired. It is preferred, however, if such excipients maintain the overall tonicity of the amylin or amylin agonist. An excipient may be included in the presently described formulations at various concentrations. For example, an excipient may be included in the concentration range from about 0.02% to about 20% w/w, preferably between about 0.02% and 0.5% w/w, about 0.02% to about 10% w/w, or about 1% to about 20% w/w. In addition, similar to the present formulations themselves, an excipient may be included in solid (including powdered), liquid, semi-solid or gel form.

In another aspect, the present formulations may be composed in various forms, e.g., solid, liquid, semisolid or liquid. The term "solid", as used herein, is meant to encompass all normal uses of this term including, for example, powders and lyophilized formulations. In a related aspect, the presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the present peptide formulations, for example, water or an aqueous/organic solvent mixture or suspension.

The stability of a peptide formulation of the present invention is enhanced by maintaining the pH of the formulation in the range of about 3.0 to about 7.0 when in liquid form. Preferably, the pH of the formulation is maintained in the range of about 3.5 to 5.0, or about 3.5 to 6.5, most preferably from about 3.7 to 4.3, or about 3.8 to 4.2. A frequently preferred pH may be about 4.0. While not seeking be bound by theory, it is presently understood that where the pH of the pharmaceutical formulation exceeds 5.5, chemical degradation of the peptide may be accelerated such that the shelf life is less than about two years.

The buffer used in the practice of the present invention is an acetate buffer (preferably at a final formulation concentration of from about 1-5 to about 60 mM), phosphate buffer preferably at a final formulation concentration of from about 1-5 to about to about 30 mM) or glutamate buffer (preferably at a final formulation concentration of from about 1-5 to about to about 60 mM). The most preferred buffer is acetate (preferably at a final formulation concentration of from about 5 to about 30 mM).

A stabilizer may be included in the present formulation but, and importantly, is not necessarily needed. If included, however, a stabilizer useful in the practice of the present invention is a carbohydrate or a polyhydric alcohol. The present inventors have discovered that a suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with amylins in non-diabetic applications (e.g. treating obesity).

Preferably, if a stabilizer is included, the peptide of the present invention is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol. Another useful feature of the lyophilized formulations of the present invention is the maintenance of the tonicity of the lyophilized formulations described herein with the same formulation component that serves to maintain their stability. Mannitol is the preferred polyhydric alcohol used for this purpose.

The United States Pharmacopoeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide. Thus, even selection of a preservative can be difficult.

While the preservative for use in the practice of the present invention can range from 0.005 to 1.0% (w/v), the preferred range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid.

A detailed description of each preservative is set forth in "Remington's Pharmaceutical Sciences" as well as *Pharmaceutical Dosage Forms: Parenteral Medications*, Vol. 1, 1992, Avis et al.

Pramlintide (previously referred to as "AC-137") does not have a tendency to adsorb onto the glass in a glass container when in a liquid form, therefore, a surfactant is not required to further stabilize the pharmaceutical formulation. However, with regard to amylin agonists or amylins which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio] 1-propanesulfonate), Brij® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations must be isotonic or substantially isotonic otherwise significant irritation and pain would occur at the site of administration.

The vehicle of greatest importance for parenteral products is water. Water of suitable quality for parenteral administration must be prepared either by distillation or by reverse osmosis. Only by these means is it possible to separate adequately various liquid, gas and solid contaminating substances from water. Water for injection is the preferred aqueous vehicle for use in the pharmaceutical formulation of the present invention.

It is possible that other ingredients may be present in the peptide pharmaceutical formulation of the present invention. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type 1-33) or its equivalent (Wheaton Glass Co.). Other vendors of similar borosilicate glass vials and cartridges acceptable for manufacture include Kimbel Glass Co., West Co., Bünder Glas GMBH and Forma Vitrum. The biological and chemical properties of amylin may be stabilized by formulation and lyophilization in a Wheaton Type 1-33 borosilicate serum vial to a final concentration of 0.1 mg/ml and 10 mg/ml of amylin in the presence of 5% mannitol, and 0.02% Tween 80.

In order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. These stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in *Pharmaceutical Dosage Forms: Parenteral Medications*, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (preservative followed by stabilizer/tonicity agents, buffers and pramlintide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 µm and 0.22 µm (1 or 2) which may be connected in series. After filtration, the solution is filled into appropriate vials or containers.

The liquid pharmaceutical formulations of the present invention are intended for parenteral administration. Suitable routes of administration include intramuscular, intravenous, subcutaneous, intradermal, intraarticular, intrathecal and the like. The subcutaneous route of administration is preferred. Mucosal delivery is also preferred. These routes include, but are not limited to, oral, nasal, sublingual, pulmonary and buccal routes which may include administration of the peptide in liquid, semi-solid or solid form. Administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. These dosage forms would typically have a lower bioavailability due to entrapment of some of the peptide in the polymer matrix or device. See e.g., U.S. Pat. Nos. 6,379,704, 6,379,703, and 6,296,842.

Some formulations of the present invention are especially advantageous because they retain short term mixing compatibility with insulin, or in the case of insulins formulated at similar pH, for longer term storage. Currently, there are over thirty insulin products available in the United States. All regular insulin preparations in the United States are now supplied at neutral pH. This has resulted in improved stability of the hormone, and patients need no longer refrigerate the vial of insulin in use. Furthermore, neutral regular insulin can be mixed in any desired proportion with other, modified insulin preparations since all marketed insulin preparations will be at the same pH. Preparations of insulin have been divided into three general categories according to promptness, duration, and intensity of action following subcutaneous administration. They are classified as fast-, intermediate-, and long-acting insulins. There are also various types of insulins within these categories. They include regular insulins, protamine zinc insulins, NPH insulins, semilente insulins (prompt insulin zinc suspensions), lente insulins (insulin zinc suspensions), and ultralente insulins (extended insulin zinc suspensions). Recently, a new type of insulin, insulin glargine (Lantus®), formulated at a pH of approximately 4.0 has become available, and may allow for longer term storage of peptide-insulin mixtures.

Crystalline insulin is prepared by the precipitation of the hormone in the presence of zinc (as zinc chloride) in a suitable buffer medium. Crystalline insulin when dissolved in water is also known as regular insulin. Following subcutaneous injection it is rapidly absorbed (15-60 minutes). Its action is prompt in onset and relatively short in duration, i.e., it reaches its peak effect in about 1.5 to 4 hours, and lasts for about 5-9 hours.

By permitting insulin and zinc to react with the basic protein protamine, Hagedorn and associates prepared a protein complex, protamine zinc insulin. When this complex is injected subcutaneously in an aqueous suspension, it dissolves only slowly at the site of deposition, and the insulin is absorbed at a retarded but steady rate. Protamine zinc suspension insulin has largely been replaced by isophane insulin suspension, also known as NPH insulin; the N denotes a neutral solution (pH 7.2), the P refers to the protamine zinc insulin content, and the H signifies the origin in Hagedorn's laboratory. It is a modified protamine zinc insulin suspension that is crystalline. The concentrations of insulin, protamine, and zinc are so arranged that the preparation has an onset and a duration of action intermediate between those of regular insulin and protamine zinc insulin suspension. Its effects on blood sugar are indistinguishable from those of an extemporaneous mixture of 2 to 3 units of regular insulin and 1 unit of protamine zinc insulin suspension.

Chemical studies have revealed that the solubility of insulin is determined in important measure by its physical state (amorphous, crystalline, size of the crystals) and by the zinc content and the nature of the buffer in which it is suspended. Insulin can thus be prepared in a slowly absorbed, slow-acting form without the use of other proteins, such as protamine, to bind it. Large crystals of insulin with high zinc content, when collected and resuspended in a solution of sodium acetate-sodium chloride (pH 7.2 to 7.5), are slowly absorbed after subcutaneous injection and exert an action of long duration. This crystal preparation is named extended insulin zinc suspension (ultralente insulin). Amorphous insulin precipitated at high pH is almost as rapid in onset as regular insulin, but has a somewhat longer duration of action. This amorphous preparation is named prompt insulin zinc suspension (semilente insulin). These two forms of insulin may be mixed to yield a stable mixture of crystalline (7 parts) and amorphous (3 parts) insulin—called insulin zinc suspension (lente insulin)—that is intermediate in onset and duration of action between semilente and ultralente preparations and is similar to NPH insulin.

In summary, the fast-acting insulins include the regular insulins and the prompt insulin zinc suspensions (semilente insulins). The intermediate-acting insulins include the isophane insulin suspensions (NPH insulins, isophane insulin) and the insulin zinc suspensions (lente insulins). The long-acting insulins include protamine zinc insulin suspensions, and extended insulin zinc suspensions (ultralente insulins). Most of these preparations are available as either porcine or bovine insulins. Human insulins of recombinant DNA origin are available as regular and isophane insulins and as insulin zinc suspensions. Recently, a modified insulin (Lys(B28), Pro(B29) human insulin analog, created by reversing the amino acids at positions 28 and 29 on the insulin B-chain) has been introduced. It is a fast-acting insulin, with a more rapid onset of glucose lowering action, an earlier peak action, and a shorter duration of action than regular human insulin.

Many insulins are available from a number of companies. These include Eli Lilly & Company and Novo Nordisk, two of the largest suppliers of insulin in the world. Fast-acting insulins available from Eli Lilly include (1) Iletin® I (Regular); (2) Regular Iletin® II (Pork, 100 Units); (3) Regular Iletin® II (Concentrated, Pork, 500 Units); (4) Humalog® Injection (insulin lyspro, recombinant DNA origin); and (5) Humulin® R (regular insulin, recombinant DNA origin, 100 Units). Fast-acting insulins available from Novo Nordisk include (1) Novolin® R (Regular, Human Insulin Injection (recombinant DNA origin) 100 Units); (2) Novolin® R PenFill 1.5 ml Cartridges (Regular, Human Insulin Injection (recombinant DNA origin) 100 Units); (3) Novolin® R Prefilled™ (Regular, Human Insulin Injection (recombinant DNA origin) in a 1.5 ml Prefilled Syringe, 100 units/ml); (4) Regular Purified Pork Insulin (100 Units/ml); and (5) Velosulin® BR (Buffered Regular Human Insulin Injection, 100 Units/ml). Intermediate-acting insulins available from Eli Lilly include (1) Humulin® 50/50 (50% human insulin isophane suspension and 50% human insulin injection (rDNA origin), 100 Units); (2) Humulin® 70/30 (70% human insulin isophane suspension and 30% human insulin injection (rDNA origin), 100 Units); (3) Humulin® L (lente; human insulin (rDNA origin) zinc suspension, 100 Units);); (4) Humulin® N(NPH; human insulin (rDNA origin) isophane suspension, 100 Units); (5) Lente® Iletin® I, (insulin zinc suspension, beef-pork); (6) NPH Iletin® I (isophane insulin suspension, beef-pork); (7) Lente Iletin® II NPH (insulin zinc suspension, purified pork); and (8) NPH Iletin® II, (isophane insulin suspension, purified pork). Intermediate-acting insulins available from Novo Nordisk include (1) Novolin® L (Lente, Human Insulin Zinc Suspension (recombinant DNA origin), 100 Units/ml); (2) Novolin® N(NPH, Human Insulin Isophane Suspension (recombinant DNA origin), 100 Units/ml); (3) Novolin® N PenFill® 1.5 ml Cartridges; (4) Novolin® N Prefilled™ (NPH, Human Insulin Isophane Suspension (recombinant DNA origin) in a 1.5 ml Prefilled Syringe, 100 Units/ml); (5) Novolin® 70/30 (70% NPH, Human Insulin Isophane Suspension and 30% Regular, Human Insulin Injection (recombinant DNA origin), 100 Units/ml); (6) Novolin® 70/30 PenFill® 1.5 ml Cartridges; (7) Novolin® 70/30 Prefilled™ (70% NPH, Human Insulin Isophane Suspension and 30% Regular, Human Insulin Injection (recombinant DNA origin) in a 1.5 ml Prefilled Syringe, 100 Units/ml); (8) Lente Purified Pork Insulin (Zinc Suspension, U.S. Pat. No. 100 Units/ml); and (9) NPH Purified Pork Isophane Insulin Suspension (100 Units/ml). Long acting insulins include Eli Lilly's Humulin® U (Ultralente® human insulin (recombinant DNA origin) extended zinc suspension); and insulin glargine (Lantus®)(Aventis).

This invention provides unique peptide formulations, preferably pramlintide or other amylin agonist peptide formulations, which facilitate the short-term mixing compatibility of all types of insulin products including regular insulin products (e.g., Humulin® R and Novolin® R), intermediate-acting insulin products (e.g., Humulin® 70/30 and Novolin® 70/30) and long-acting insulin products (e.g., Humulin® U) with the peptide formulation before administration. The desired bioavailability of insulin and amylin agonist peptide or amylin is maintained. This results in a significant reduction in the number of injections per day in patients who are undergoing treatment with insulin and an amylin agonist (e.g., pramlintide) or amylin.

Insulin as well as insulin analogs are useful in the practice of the present invention. Monomeric insulin analogs have been developed, e.g., $Lys^{B28}Pro^{B29}$-human insulin, which is also referred to as "LysPro insulin" or "insulin lispro." These analogs are said to be advantageous because they can be stabilized by ligands which induce the otherwise monomeric analog to associate under pharmaceutically useful conditions. This stabilized analog remains fast acting in an associated state.

Thus, any type of insulin may be drawn into a syringe along with the peptide formulation of the present invention. Any order of mixing or introduction of peptide and insulin into a syringe is also possible, such as simultaneous or concerted and sequential admixing, but the preferred order is to place the insulin in the syringe first, followed by peptide in order to reduce the potential for cross-contamination and precipitation.

The amount of insulin and peptide formulation in the syringe depends on the individual needs of a particular patient. Accordingly, the amount present in a syringe is an amount sufficient to maintain a proper insulin level for a patient. The pharmaceutical formulations of the present invention can be administered to any human or mammal in need of such treatment.

As has been demonstrated with pramlintide, and depending upon the type of insulin and the volume ratio of the mixture, the insulin and peptide formulation can remain in the same syringe for at least about 24 hours and the insulin and the peptide will retain their activity and stability.

For instance, regular insulin products may be mixed with a peptide, e.g., pramlintide, at a pH of approximately 4.0 with 20 or 30 mM acetate buffer to maintain the solubility of the insulin. The pH of the mixture would then be less than 4.5. A preferred peptide formulation of pramlintide with a higher buffer capacity (30 mM acetate) and at low label strength, e.g., 0.1 mg/ml, forms a clear solution instantaneously (under a minute) when mixed with regular insulin products in the range of five to 20 units. This low label strength of pramlintide results in a high dose volume, 300 μL. This increased volume may be advantageous for bringing the pH down to less than 4.5 almost immediately by increasing insulin dilution factor and facilitating the transition of insulin from hexamer to monomer before injection. This modulation of insulin is believed to be advantageous in permitting increased rate of absorption and causing rapid-time action without affecting bioavailability of insulin. This effect may approach the rapid-time action observed in $Lys^{B28}Pro^{B29}$ human insulin.

Peptide formulations, e.g., pramlintide, at a pH from 4.0 to 5.5, 2 to 30 mM buffer concentration and high potency, can be mixed with regular insulin products before injection to yield solutions with a pH greater than 6.8 so that the properties of insulin are not affected. These mixtures would not affect the rate of absorption or bioavailability of insulin nor the bioavailability of the peptide.

An alternative to mixing of the peptide with insulin prior to administration is to utilize a two chambered cartridge or syringe. In such a system, the peptide (e.g. pramlintide) is filled during manufacturing into one cartridge or syringe chamber in contact with the plunger. In this cartridge or syringe, a divider comprised of rubber or another suitable material known in the art, preferably isolates the solution of peptide contained in the first chamber from the second chamber. Prior to administration, the needed amount of insulin is measured into the second chamber. Preferably, the insulin is measured into the two chambered cartridge or syringe immediately prior to administration to a subject. When both chambers are filled with the appropriate amount of peptide and insulin, the two chambers may be administered to a subject, together or in series.

Another alternative is the formulation of peptide for use with insulin pumps. Patients using insulin pumps frequently must administer an extra dose of insulin in close proximity to meals. Amylin peptides are typically also administered at this time. Formulations of amylin peptide can be filled into cartridges or syringes or other devices that allow the user of an insulin pump to co-administer the peptide as needed.

Formulations of the invention are generally described above. Below are provided examples of various formulations useful in the invention. These examples are not limiting to the invention and those of ordinary skill in the art can readily construct other formulations within the ambit of the claims.

The invention will now be described in greater detail by reference to the following non-limiting examples.

EXAMPLES

Example 1

Liquid Pramlintide Formulation

Figure 1:
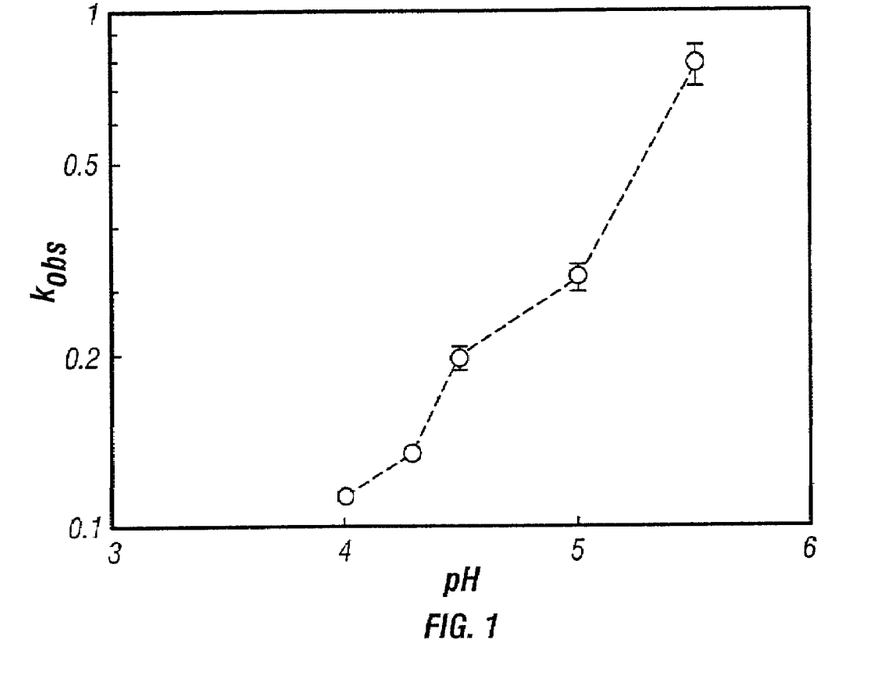
FIG. 1 shows the degradation rates of pramlintide at various pH formulations.

This example describes two preferred liquid formulations for pramlintide. Major degradation pathways for the peptide are deamination and peptide bond hydrolysis. Therefore, the stability of the peptide was investigated in the pH region of 4.0-5.5 at 45° C. The pH-rate profile for the peptide in 60 mM acetate buffer, 4.1% mannitol, 0.3% m-cresol is shown in FIG. 1. It can be observed from this figure that Pro$^{25,28,29}$h-amylin over the pH range studied is most stable at pH 4.0. The following formulation was developed:

TABLE A

| INGREDIENT | Weight (%)/Range |
|---|---|
| Pramlintide Acetate(30 mM, pH 4.0 ± 0.1): | 0.01-0.2 |
| sodium acetate trihydrate | 0.061 |
| glacial acetic acid | 0.153 |
| mannitol | 4.3 |
| m-cresol | 0.225 |
| Water For Injection (qs) | 100 mL |

The above formulation with 0.01% drug showed an acceptably low irritancy in a rabbit subcutaneous irritancy study. The placebo of this formulation when tested in humans also showed an acceptably high level of tolerability and low irritancy. The preservative used in the formulation meets BP criteria for preservative efficacy at m-cresol levels as low as 0.15%.

Figure 2:
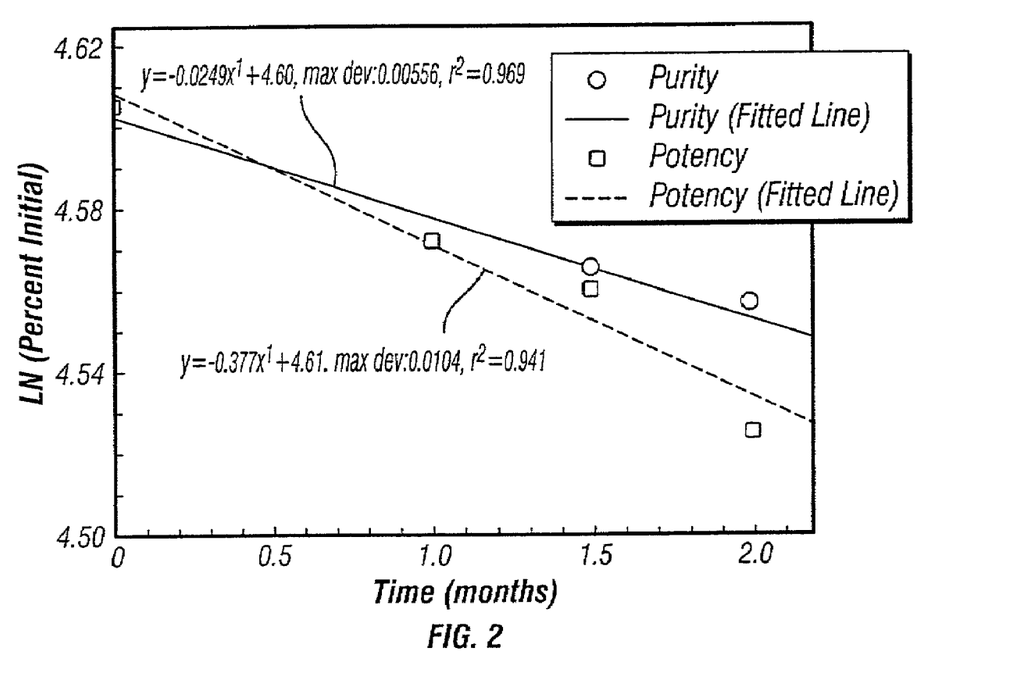
FIG. 2 shows the stability of the pramlintide formulation over time at 30° C.
Figure 3:
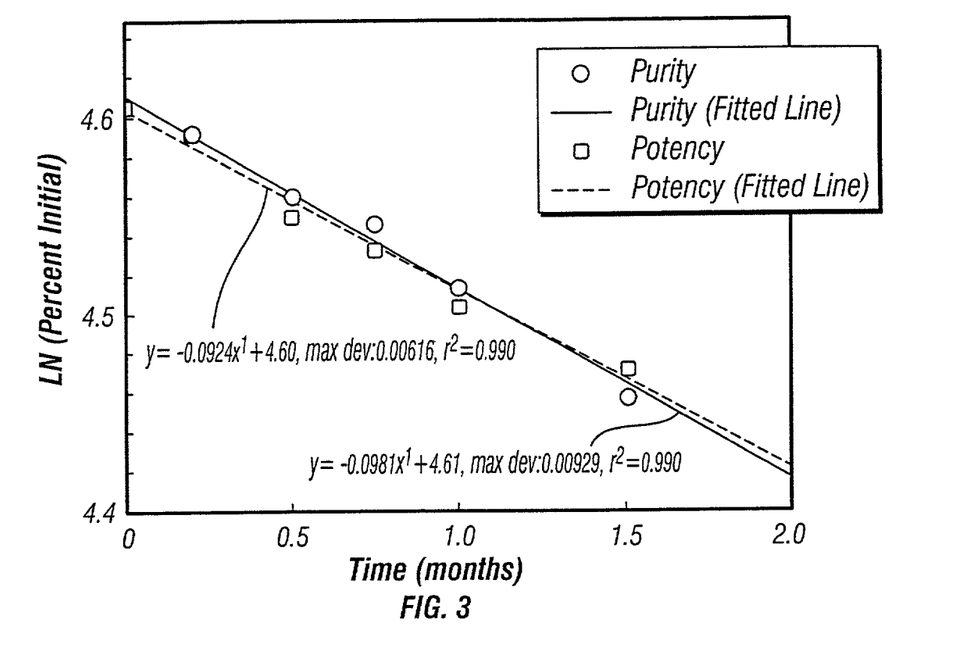
FIG. 3 shows the stability of the pramlintide formulation over time at 40° C.
Figure 4:
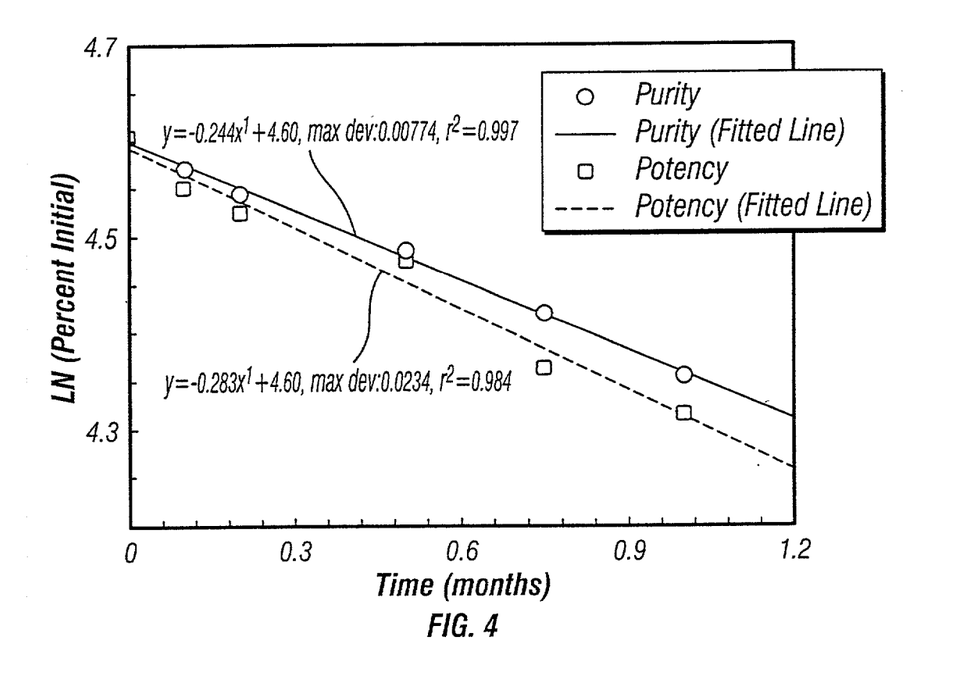
FIG. 4 shows the stability of the pramlintide formulation over time at 50° C.
Figure 5:
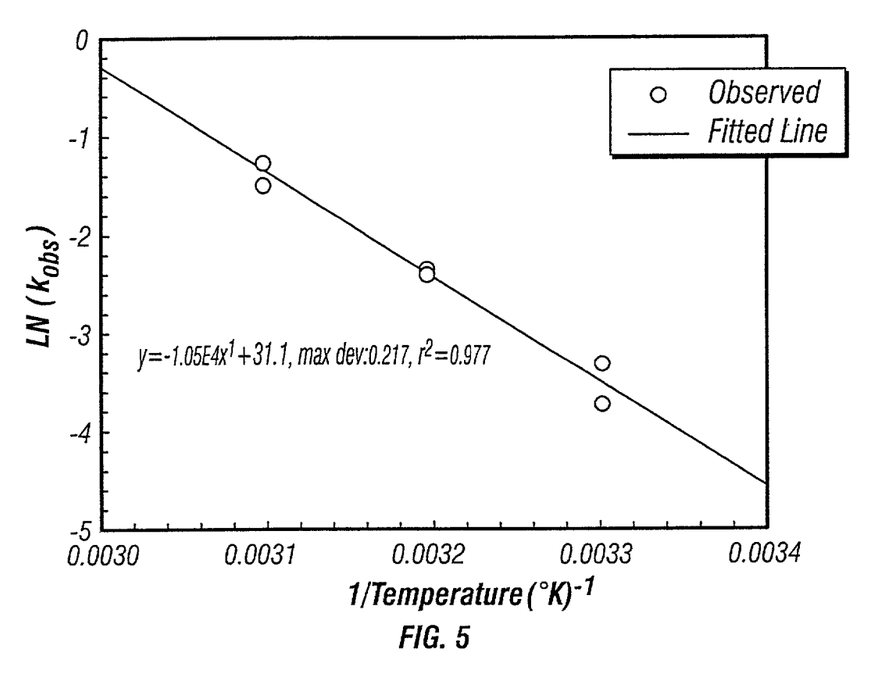
FIG. 5 shows an Arrenhius plot of the $K_{obs}$ values from FIGS. 2-4.

The stability of the above formulation with 0.01% peptide was evaluated at 4° C. and accelerated conditions, 30° C., 40° C. and 50° C. Based on strong cation exchange HPLC analysis for purity and potency, semi-logarithmic plots of % Initial purity or potency versus time for the peptide were constructed as shown in FIGS. 2, 3 and 4. It can be observed that the degradation of the peptide follows pseudo-first order or zero order kinetics and that the degradation rate (represented by slopes of these plots), increases significantly with an increase in temperature. FIG. 5 shows plot of $\ln(k_{obs})$ versus 1/Temperature, constructed based on the Arrhenius relationship. It can be observed from this plot that the degradation of pramlintide in the formulation follows Arrhenius kinetics. By extrapolation of the plot to 5° C. rate constant was calculated and shelf-life of up to four years for the peptide was predicted using this rate constant. Approximately 10% loss of potency and/or 5% to 7% degradation was considered acceptable. The shelf-life of the pharmaceutical formulation at 30° C. based on direct measurement is at least 60 days.

Example 2

Liquid Pramlintide Formulation

Table B describes second the peptide formulation with a shelf-life of greater than 4 years at 4° C. and greater than 60 days at 30° C. This formulation differs from the one in Table A in acetate buffer concentration. This formulation also showed no irritancy in a rabbit subcutaneous irritancy study. Additionally, the placebo did not show significant irritancy in humans. The shelf-lives of these formulations are at least as great as the formulation given in Table A, both formulations being novel parenteral peptide dosage forms with substantial shelf-lives.

TABLE B

| INGREDIENT | Weight (%)/Range |
|---|---|
| Pramlintide Acetate (20 mM, pH 4.0 ± 0.1): | 0.01-0.2 |
| sodium acetate trihydrate | 0.049 |
| glacial acetic acid | 0.0985 |
| mannitol | 4.3 |
| m-cresol | 0.225 |
| Water for injection (qs) | 100 mL |

Example 3

Liquid Pramlintide Formulation and Insulin

The formulations reported in Tables A and B are also compatible when mixed in a syringe with commercially available insulin products. Table C provides results of insulin compatibility study with Humulin® R. The results indicate the time to form a clear solution and criteria for compatibility, when the peptide formulation is mixed with Humulin R in a specific ratio in a syringe. As outlined by Brange et al, "Insulin Structure and Stability," in *Stability and Characterization of Protein and Peptide Drugs: Case Histories*, 1993, Wang et al. (Ed), Plenum Press, NY, insulin has an isoelectric precipitation zone pH range of 4.5-6.5, within 1 pH unit from isoelectric point. Therefore, while not seeking to be bound by theory, if the pH of the insulin product drops from 7.2±0.2 to pH in the isoelectric precipitation range it may cause insulin to precipitate. Thus, clarity of the solution mixture was used as a criteria for preliminary compatibility studies. The insulin volumes used in this study (Table C) cover the maximum and minimum ranges typical for Type I diabetic patients. The formulation with higher buffer capacity (Table C) forms a clear solution faster than the lower buffer capacity formulation. However, at 0.01% of the peptide label strength both formulations form a clear solution with insulin within approximately one minute. In a syringe, one minute can be considered to be instantaneous mixing. The higher label strength of the peptide (0.015% or higher) results in lower dose volume and may require longer than a minute to form a clear solution. The final pH of all solution mixtures fall outside of insulin isoelectric precipitation range (pH 4.5-6.5).

TABLE C

| Pramlintide Formulation Variants | | Insulin: Pramlintide | | Time to Form |
|---|---|---|---|---|
| Label Strength (%) | Acetate (mM) | Mixing Volume Ratio (μL:μL) | pH of the Mixutre | Clear Solution (sec) |
| 0.01 | 30 | 50 (5 units):300 | 4.03 | 0 |
| | | 150:300 | 4.10 | 15 |
| | | 200:300 | 4.13 | 35 |
| | 20 | 50:300 | 4.09 | 0 |
| | | 150:300 | 4.15 | 22 |
| | | 200:300 | 4.20 | 60 |
| 0.015 | 30 | 50:200 | 4.05 | 0 |
| | | 150:200 | 4.12 | 99 |
| | | 200:200 | 4.24 | 192 |
| | 20 | 50:200 | 4.13 | 10 |
| | | 150:200 | 4.27 | 197 |
| | | 200:200 | 4.30 | 300 |

Figure 6:
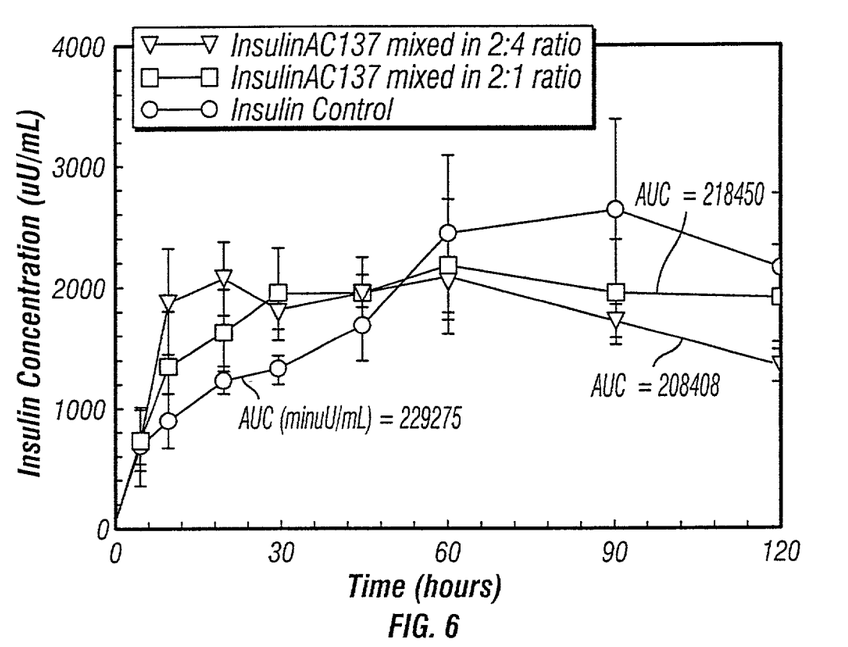
FIG. 6 shows plasma concentrations versus time for insulin following mixing the amylin agonist peptide pramlintide formulated according to Table A.

The formulation with 0.03% label strength (Table A) was subjected to in vivo compatibility study in rats. FIG. 6 shows the plasma concentration versus time for insulin. The study indicated no significant differences in the bioavailability of either insulin or peptide when injected together after mixing or separately as individual injections. Therefore, these novel formulations are not only stable but also compatible with regular insulin products such as, Humulin® R and Novolin® R.

The preferred formulations (Tables A and B) were also tested for compatibility with intermediate acting (Humulin® 70/30) and long acting (Humulin® N) insulin products. These two insulin products are suspensions and they both contain soluble and insoluble insulin portions in specific ratios, and these ratios are required to achieve targeted bioavailability. Therefore, when mixed with the peptide formulation the ratio of soluble to insoluble insulin is preferably maintained. The sample preparation to separate soluble to insoluble portions from peptide/insulin mixtures was adopted from Arakawa et al., *Diabetes Research and Clinical Practice*, 1989. Samples were analyzed using a reverse phase HPLC assay. Table D summarizes the results of the study. Both formulations maintain the soluble to insoluble ratios as in control formulations when Humulin® 70/30 and Pro$^{25,28,29}$h-amylin formulations are mixed in a 3:1 ratio. Therefore, in a preferred formulation the dose volume should be maintained by choosing an appropriate peptide label strength. For example, using 0.6 mg/mL or 0.06% label strength formulation to mix with 15 units of Humulin 70/30.

TABLE D

| Pramlintide Formulation Variants (Label Strength: 0.3 mg/mL or 0.03%) | | Insulin: | pH of | Percent | |
|---|---|---|---|---|---|
| pH | Acetate (mM) | Pramlintide Ratio (μL:μL) | the Mixture | Soluble Insulin | % Soluble Pramlintide |
| 4.0 | 20 | 300(30 Units):100 | 6.77 | 12 | 101 |
|  |  | 150:100 | 5.74 | 4 | 100 |
| 4.0 | 30 | 300:100 | 6.41 | 10 | 97 |
|  |  | 150:100 | 5.15 | 4 | 98 |
| Humulin N:Humulin R (70:30) (control) | | N/A | 7.12 | 11 | N/A |
| Premixed Humulin 70/30 (control) | | 100:0 | 7.46 | 16 | N/A |

Table E shows compatibility data for formulations with long acting insulin product, Humulin® N. The Humulin® N covers a normal dosage range for Type I diabetic patients. The soluble to insoluble ratios do not change significantly compared to the control when preferred formulations, in Tables A and B, are mixed with Humulin®0 The preferred peptide dose volume is 100 μL.

The formulations described in Tables A and B of Example 1 are preferred formulations with necessary stability and insulin compatibility requirements.

TABLE E

| Pramlintide Formulation Variants (Label Strength: 0.3 mg/mL or 0.03%) | | Insulin: | pH of | Percent | |
|---|---|---|---|---|---|
| pH | Acetate (mM) | Pramlintide Ratio (μL:μL) | the Mixture | Soluble Insulin | % Soluble Pramlintide |
| 4.0 d | 20 | 160(16 Units):100 | 5.51 | 2 | 100 |
|  |  | 120:100 | 5.10 | 4 | 105 |

TABLE E-continued

| Pramlintide Formulation Variants (Label Strength: 0.3 mg/mL or 0.03%) | | Insulin: | pH of | Percent | |
|---|---|---|---|---|---|
| pH | Acetate (mM) | Pramlintide Ratio (μL:μL) | the Mixture | Soluble Insulin | % Soluble Pramlintide |
| 4.0 | 30 | 160:100 | 5.06 | 3 | 99 |
|  |  | 120:100 | 4.82 | 4 | 97 |
| Humulin N (control) | | 100:0 | 7.20 | 2 | N/A |

As provided above, a co-formulation with insulin glargine, formulated at approximately pH 4.0, provides an alternative mixture which exhibits long term stability and allows for storage of the formulation for greater than 24 hours.

Example 4

Liquid Peptide Formulation and Insulin

The formulation in this example is the preferred formulation for mixing with intermediate acting (Humulin® 70/30 & Novolin® 70/30) and long acting (Humulin® N and Novolin® N) insulin products.

TABLE F

| INGREDIENT | Weight (%)/Range |
|---|---|
| Pramlintide | 0.03 |
| Acetate (12 mM, pH 4.4) |  |
| sodium acetate trihydrate | 0.0555 |
| glacial acetic acid | 0.0476 |
| mannitol | 4.4 |
| m-cresol | 0.225 |
| Water for injection (qs) | 100 mL |

The stability of this formulation is 3.3 years at 5° C., calculated by extrapolation using accelerated stability data, and found to be 33 days at 30° C. using the real time data. The insulin compatibility studies with Humulin® 70/30 and Humulin® N were conducted following the procedure outlined in Example 3. The formulation maintains insulin soluble to insoluble ratios in the range of controls when mixed with Humulin® 70/30 (Table G) or Humulin® N (Table H). The pH of the mixture does not deviate from the control samples.

TABLE G

| Pramlintide Formulation Variants mg/mL or 0.03%) | | Insulin: Pramlintide | pH of the | % Percent | Soluble |
|---|---|---|---|---|---|
| pH | Acetate (mM) | Ratio (μL:μL) | Mixture | Soluble Insulin | Pramlintide |
| 4.4 | 12 | 300:100 | 7.02 | 13 | 88 |
|  |  | 150:100 | 6.82 | 11 | 92 |
| Humulin ® N:Humulin ® R (70:30) (Control) | | N/A | 7.12 | 11 | N/A |
| Premixed Humulin ® 70/30 (Control) | | 100:0 | 7.46 | 16 | N/A |

TABLE H

| Parmlintide Formulation Variants (Label Strength: 0.3 mg/mL or 0.03%) | | Insulin: Pramlintide Ratio | pH of the Mixture | Percent Soluble Insulin | % Soluble Pramlintide |
|---|---|---|---|---|---|
| Ph | Acetate (mM) | (µL:µL) | | | |
| 4.4 | 12 | 160:100 | 6.54 | 3 | 99 |
| | | 10:100 | 6.26 | 1 | 99 |
| Humulin ® N (Control) | | 100:0 | 7.20 | 2 | N/A |

Example 5

Liquid Pramlintide Formulation

This is a formulation with low buffer concentration, 10 mM of acetate buffer and pH closer to physiological pH compared to the formulations in examples 1-4. While not seeking to be bound by theory, the stability of this formulation is calculated by extrapolation to be 2.76 years 5° C. based on accelerated stability data and found to be at least 32 days at 30° C. using real time data.

TABLE I

| INGREDIENT | Weight (%)/Range |
|---|---|
| Pramlintide | 0.01-0.4 |
| Acetate (10 mM, pH 4.7) | |
| sodium acetate trihydrate | 0.066 |
| glacial acetic acid | 0.0309 |
| mannitol | 4.5 |
| m-cresol | 0.225-0.3 |
| Water for injection (qs) | 100 mL |

Example 6

Lyophilized Peptide Formulation

Amylin agonists may be stabilized by lyophilization. In addition, amylin agonist formulations described herein may be stabilized by lyophilization. For example, see the formulation listed in Table J. This formulation is intended for amylin agonists or amylins having physicochemical characteristics that include lower solubility and/or higher instability.

Pramlintide, however, a superior amylin agonist peptide, may also be lyophilized in a formulation, e.g., listed in Table J.

TABLE J

| INGREDIENT | WEIGHT (%)/RANGE |
|---|---|
| Amylin Agonist | 0.03-1.0 |
| Mannitol | 5.0 |
| Polysorbate 80 | 0.02 |
| Water for Injection (qs) | 100 ml |

Example 7

Liquid Peptide Formulation

Amylin agonists such as pramlintide may be minimally formulated with 30 mM acetate buffer as described in Table K.

TABLE K

| INGREDIENT | WEIGHT (%)/RANGE |
|---|---|
| Pramlintide | 0.01-0.5 |
| Glacial Acetic Acid | 0.153 |
| Sodium Acetate Trihydrate | 0.061 |

Example 7

Liquid Peptide Formulation

Amylin agonists such as pramlintide may be minimally formulated with a buffer. In addition, a penetration enhancer, a preservative or a polymer may be added individually or in some combination to facilitate nasal or buccal delivery in a liquid drop or spray, as described in Table L. Alternate buffer systems, known in the art, can also be used.

TABLE L

| INGREDIENT | WEIGHT (%)/RANGE |
|---|---|
| Pramlintide | 0.01-1.0 |
| Glacial Acetic Acid | 0.153 |
| Sodium Acetate Trihydrate | 0.061 |
| Penetration enhancer | As needed. |
| Preservative | As needed. |
| Polymer | As needed. |

A composition suitable for buccal, pulmonary and/or sublingual delivery can be produced by formulating a solid dosage form with solid peptide (i.e., a tablet), through lyophilizing the peptide formulation of Table L to produce a solid form or adsorbing this formulation on to a solid carrier (e.g. a powdered excipient, such as lactose) or a polymer, a polymer mixture or a polymeric substrate, if needed. See A. R. Gennaro et al., 17th Remington's "Pharmaceutical Sciences."

Any of the above described processes of formulating a solid dosage form will be suitable to produce sublingual tablets which dissolve rapidly and deliver the solid peptide to the mucosa under the tongue.

Pulmonary delivery is typically facilitated by inhalation of a fine powder formulation or fine liquid droplets. In some cases, a surfactant or enzyme inhibitor is included in the fine powder formulation to prevent or slow the chemical degradation of the peptide when in contact with biological tissues.

Formulations for transdermal delivery can be solid (e.g., powder), semi-solid, or liquid, and can be delivered via any suitable technology, for example as described in U.S. Pat. Nos. 6,183,434, 6,142,939, 6,173,202, and related patents.

TABLE M

| INGREDIENT | WEIGHT (%)/RANGE |
|---|---|
| Pramlintide | 0.01-90% |
| Lactose | 1.0-20% |
| Stabilizer or enzyme inhibitor | As needed. |
| Penetration enhancer | As needed. |
| Preservative | As needed. |
| Polymer | As needed. |

Buccal formulations can be prepared in a similar manner as the solid formulations described above, but with the addition of bioadhesive polymers or related formulations that allow the dosage formulation to adhere to the buccal mucosa. See e.g., U.S. Pat. No. 6,153,211.

Producing solid dosage forms for oral or sublingual administration involves the utilization of a lyophilized or crystalline form of the peptide which is preferably blended with additional powders which are known in the art, to formulate a capsule or tablet. Preferably, the solid dosage form additionally includes an enzyme inhibitor, a complexing agent and/or stabilizer. These ingredients are useful for protection of the peptide from degradation in the gastrointestinal tract. Alternatively, the capsule or tablet may be enteric coated or coated with a polymer that releases the formulation of the peptide in a desired location in the gastrointestinal tract. See e.g., A. R. Gennaro et al., 17th Remington's "Pharmaceutical Sciences." A suitable formulation could be created by modification of the formulation in Table M in the above described manner.

Example 8

Injectable Controlled Release Formulation

It is advantageous to patients to utilize a formulation of peptide that requires administration less frequently than multiple times per day. Specifically, the peptide can be formulated in a mixture with biocompatible polymers or oils that slowly release the peptide in a timeframe from days to months. An example of these formulations are shown on Table N and O. Table N represents an injectable microsphere product and Table O represents an oil based formulation.

TABLE N

| INGREDIENT | WEIGHT (%)/RANGE |
|---|---|
| Pramlintide | 0.01-40.0 |
| Glacial Acetic Acid | 0.153 |
| Sodium Acetate Trihydrate | 0.061 |
| Sugar or polyhydric alcohol | 0.1-10% |
| Release modifier (e.g. Ammonium sulfate) | 0.005-2% |
| Polymer (e.g. PLGA) | 1-98% |

TABLE O

| INGREDIENT | WEIGHT (%)/RANGE |
|---|---|
| Pramlintide | 0.01-40.0 |
| Oil vehicle | 1-98% |
| Non-aqueous solvent | 0.01-90% |
| Sugar or polyhydric alcohol | 0.1-10% |

Any pharmaceutically acceptable emulsifiers, such as oils, may be utilized in the formulation of Table O and other similar formulations described herein. See e.g., Remington's "Pharmaceutical Sciences"; and Idson, Pharmaceutical Emulsions, Ch. 6, Pharmaceutical Dosage Forms, Disperse Systems. Vol. 1., New York, 1988.

Example 9

Transdermal Delivery

In certain instances it is beneficial to eliminate the need for injections through the use of transdermal delivery of the peptide. This may be facilitated through the formulation of the peptide into a patch or device that is attached to the skin and delivers the peptide into the skin at a desired rate.

All references cited herein are hereby incorporated by reference in their entireties, whether previously specifically incorporated or not. As used herein, the terms "a", "an", and "any" are each intended to include both the singular and plural forms and the term "or" is intended to refer to alternatives and combinations.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Citation of the above publications or documents is not intended as an admission that any of the foregoing is pertinent prior art, nor does it constitute any admission as to the contents or date of these publications or documents.

We claim:

1. A liquid pharmaceutical formulation comprising about 0.5 to 1.0% (w/v) of an amylin agonist, a pharmaceutically acceptable excipient and a liquid vehicle comprising water or an aqueous/organic solvent mixture or suspension, wherein said formulation comprises about 1.0 to 10% (w/v) of a carbohydrate or a polyhydric alcohol, about 0.02 to 0.5% (w/v) of an acetate, phosphate, citrate or glutamate buffer, and wherein the pH of said formulation is about 3.5 to about 5.0.

2. The formulation of claim 1, wherein the pH of said formulation is about 3.8 to about 4.2.

3. The formulation of claim 1 which is substantially isotonic.

4. The formulation of claim 1, wherein said amylin agonist is pramlintide.

5. The formulation of claim 1, wherein said polyhydric alcohol is mannitol, sorbitol, inositol, glycerol, xylitol, propylene/ethylene glycol copolymer. PEG 8000, PEG 400, PEG 4000, PEG 200, PEG 1450 or PEG 3350.

6. The formulation of claim 1, wherein said polyhydric alcohol is mannitol.

7. The formulation of claim 1, wherein said carbohydrate is mannose, ribose, trehalose, maltose, glycerol, inositol, lactose, sucrose, fructose, galactose, or arabinose.

8. The formulation of claim 1, wherein said formulation further comprises a surfactant.

9. The formulation of claim 8, wherein said surfactant is polyoxyethylene (20) sorbitan monooleate, 3-[(3-cholamidopropyl) dimethylammonio]1-propanol sulfonate, polyoxyethylene (23) lauryl ether, poloxamer or a non-ionic surfactant.

10. The formulation of claim 8, further comprising a preservative.

11. A method for treating diabetes in a patient in need of such treatment comprising administering a therapeutically effective amount of the formulation of claim 1 to the patient in need of such treatment.

12. The method of claim 11 wherein insulin is admixed with said formulation prior to administration.

13. The method of claim 12 wherein the admixing step is simultaneous, or concerted and sequential with administration.

14. The formulation of claim 1 for administration to a subject, wherein the formulation is administered in the form selected from the group consisting of a parenteral controlled release delivery, oral delivery, a microcapsule delivery, a microsphere, an implant delivery, and a polymer matrix delivery.

15. A liquid suspension formulation comprising about 0.5 to 90% (w/v) of an amylin agonist, about 1.0 to 10% (w/v) of a carbohydrate or a polyhydric alcohol; and about 0.02 to 0.5% (w/v) of an acetate, phosphate, citrate or glutamate buffer, and a liquid vehicle, wherein the formulation has a pH of about 3.5 to about 5.0.

16. The formulation of claim 1 formulated for nasal or pulmonary delivery.

17. The formulation of claim 1 formulated for controlled release injectable delivery.

18. The formulation of claim 1 formulated for transdermal delivery.

19. A formulation comprising about 0.5 to 1.0% (w/v) of an amylin agonist, insulin, and a pharmaceutically acceptable emulsifier, wherein said formulation comprises about 0.1 to 10% (w/v) of a carbohydrate or a polyhydric alcohol and wherein the pH of said formulation is about 3.0 to about 7.0.

20. The formulation mixture of claim 19 for use with an insulin pump device.

21. The formulation of claim 19, wherein the emulsifier is an oil.

22. The formulation of claim 19, wherein the insulin is glargine.

23. The formulation of claim 1, wherein the amylin agonist is stable for at least 30 days at room temperature.

24. The formulation of claim 15, wherein said amylin agonist is pramlintide.

25. The formulation of claim 19, wherein said amylin agonist is pramlintide.

26. The formulation of claim 1, further comprising a penetration enhancer or a stabilizer.

27. The formulation of claim 19, further comprising at least one pharmaceutically acceptable excipient selected from the group consisting of a penetration enhancer and a stabilizer.

28. The formulation of claim 1 for administration to a subject, wherein the formulation is administered in a form for controlled release delivery.

* * * * *